US00PP10008P

United States Patent [19]

Osiecki

[11] Patent Number: Plant 10,008

[45] Date of Patent: Aug. 19, 1997

[54] SPATHIPHYLLUM PLANT 'S12'

[75] Inventor: Marian W. Osiecki, Marianna, Fla.

[73] Assignee: Oglesby Plant Laboratories, Inc., Altha, Fla.

[21] Appl. No.: 638,141

[22] Filed: Apr. 26, 1996

[51] Int. Cl.[6] ..... A01H 5/00

[52] U.S. Cl. ..... Plt./88.1

[58] Field of Search ..... Plt./88.1

*Primary Examiner*—James R. Feyrer
*Assistant Examiner*—Kent L. Bell
*Attorney, Agent, or Firm*—Rothwell, Figg, Ernst & Kurz, pc

[57] ABSTRACT

A new and distinct cultivar of Spathiphyllum is provided. It is a medium size plant, relatively open, suitable for production in a 15–20 cm pot from a single tissue culture produced microcutting; grows vigorously, naturally flowers early, abundantly and year-round; has dark green, glossy, thick leaves. Long lasting, relatively large spathes of a good quality from near onset of flowering are held on thick, strong peduncles; little to no pollen production reduces the amount of foliage cleaning prior to sale.

2 Drawing Sheets

SUMMARY OF THE INVENTION

This invention relates to a new and distinct Spathiphyllum cultivar characterized by the following combination of repeatedly observed traits:

1. Medium size,
2. relatively open growth habit,
3. vigorous growth,
4. early, abundant and year-round natural flowering,
5. good quality inflorescence from near onset of flowering,
6. thick, strong peduncles and relatively large spathes on mature shoots,
7. limited pollen production,
8. dark green, glossy, thick leaves;

and primarily selected for those characteristics being so selected from the progeny of the cross stated below in a cultivated area near Altha, Fla.

ORIGIN AND ASEXUAL REPRODUCTION

The new cultivar is a product of a planned breeding program carried out at Olglesby Plant Laboratories, Inc. near Altha, Fla. The female parent was a selected clone of Spathiphyllum 'Petite' and the male parent was a selected seedling of *Spathiphyllum floribundum* designated No. 1. The cross was made in 1991, the plant was selected in 1992 and has since been reproduced by tissue culture in the vicinity of Altha, Fla. with the characteristics stated, found to be maintained through successive generations.

This new cultivar has been identified as Spathiphyllum 'S12'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'S12' was approximately 15.5 months from planting a single tissue culture produced microcutting and was grown in a 15 cm pot.

In the photographs:

DETAILED DESCRIPTION OF THE NEW CULTIVAR

Figure 1:
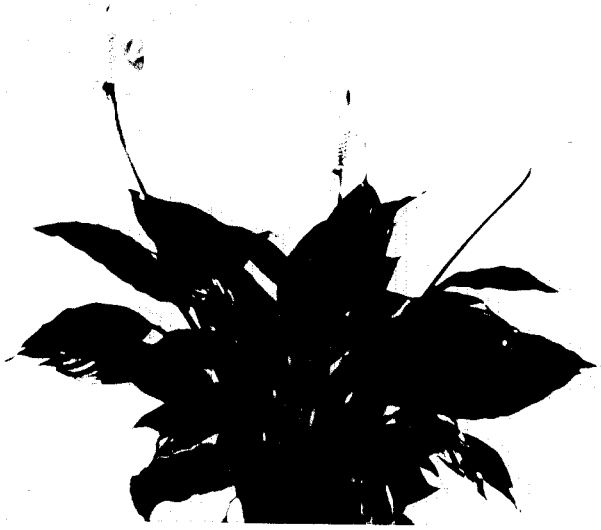
FIG. 1 depicts the whole plant.
Figure 2:
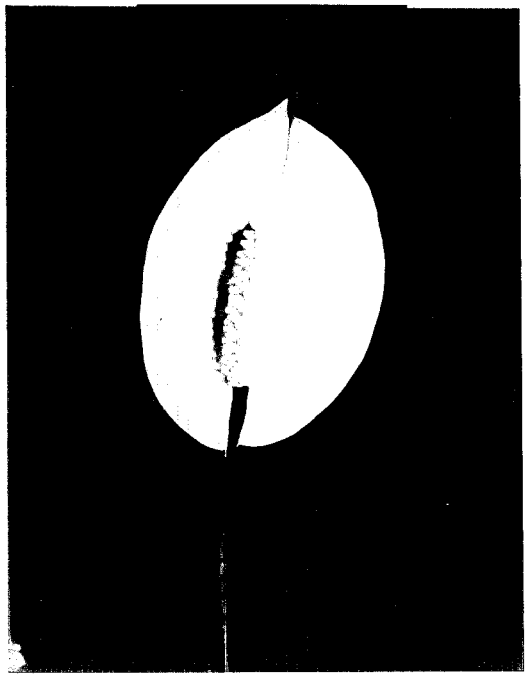
FIG. 2 illustrates the mature inflorescence.
Figure 3:
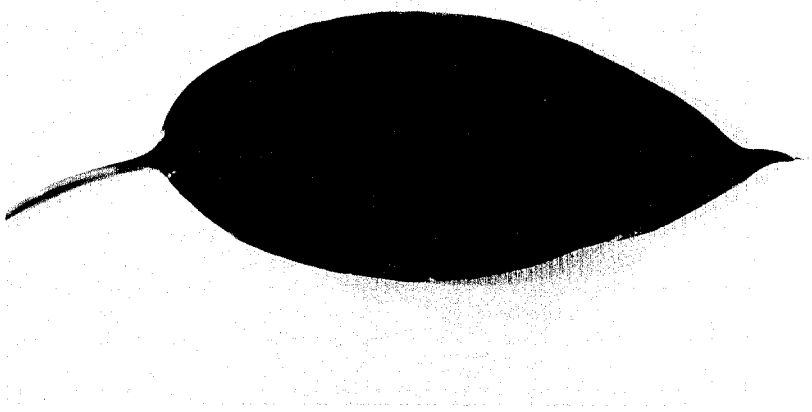
FIG. 3 illustrates the top of a mature leaf.
Figure 4:
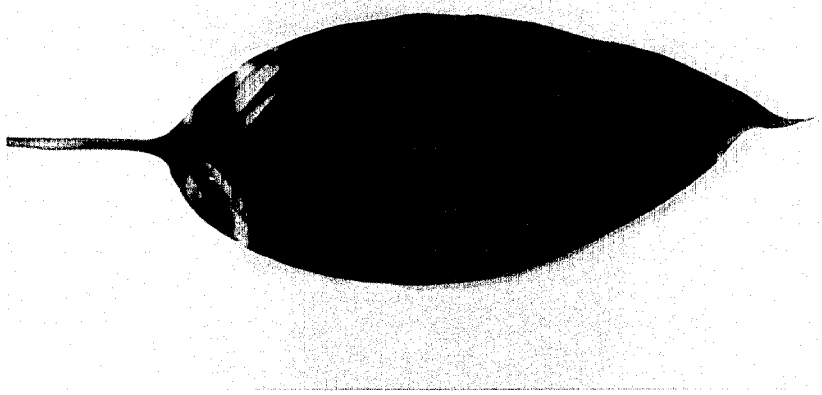
FIG. 4 illustrates the bottom of a mature leaf.

The following observations and measurements describe plants grown near Altha, Fla. under greenhouse conditions. These observations and measurements were recorded in November, 1994 from mature plants (about 12 months from planting tissue culture produced microcuttings) grown in 15 cm pots. Fully developed organs were used for measurements. Color values were determined on Nov. 17, 1994, under natural, indirect light of approximately 185 foot-candles. Color references are made to The R.H.S. Color Chart, except where general color terms of ordinary significance are used.

'S12' has not been observed under all possible environmental conditions. The phenotype may vary with variations in environment and horticultural practices, such as temperature, light intensity, day length, fertilization, propagation method, etc., without any change in genotype.

Parentage:

*Female parent.*—Selected clone of Spathiphyllum 'Petite'.

*Male parent.*—Selected seedling of *Spathiphyllum floribundum* designated No. 1.

Propagation: Plant tissue culture.

Plant:

*Growth habit.*—Medium size, relatively open.

*Height.*—Foliage 41–44 cm, with spathes 61–72 cm.

*Diameter.*—62–73 cm.

Petiole:

*Size.*—18–34.5 cm long, 3.0–4.0 mm in diameter (immediately below geniculum).

*Geniculum.*—3.0–4.0 cm long, 4.0–5.0 mm in diameter (at the base).

Leaf blade:

*Shape.*—Elliptic, sometimes with ovate tendencies, width divided slightly unequally by midrib; tip — acuminate with some aristate tendencies, often slightly curled; base — cuneate to almost obtuse, narrowly decurrent on peduncle; margin slightly wavy.

*Size.*—20.7–25.5 cm long by 8.2–10.0 cm wide; length:width ratio 2.3–2.6:1.

*Texture.*—Thick, leathery, smooth, glossy; young leaves highly polished.

*Veins.*—Well defined and sunken in the adaxial leaf surface, protruding from the abaxial leaf surface.

*Color.*—Mature leaf: Adaxial: darker than 147 A (yellow-green). Abaxial: between 147 A–B (yellow-green) and 137 A–B (green), closest to 147 B; veins 146 A–C (yellow-green). Young leaf: Adaxial: a little lighter than 137 B (green), much darker than 137 C (green). Abaxial: 137 C (green).

Inflorescence:

*Arrangement.*—Spathes on mature shoots carried on strong, straight peduncles a moderate distance above foliage. Peduncles produced by very young shoots may be weaker and thinner than those on mature shoots. Spadix prominent, situated relatively low on the spathe. Spathe length: spadix length ratio 1.9–2.6:1.

*Development.*—When spathe unrolls, spadix and the proximal spathe edges in region of spadix length are in approximately same plane with peduncle or sometimes spadix leans slightly forward. Distal spathe edges usually curve forward over spadix. At inflorescence maturity spadix is usually vertical and curving of spathe over spadix is diminished. Spathe stays cupped through senescence and only rarely leans backwards.

*Scent.*—Strong scent in the morning hours.

Peduncle:

*Size.*—48.5–62.0 cm long, 4.0–6.5 mm in diameter immediatey below spathe. At 4 to 5 cm below spathe peduncle abruptly thins by up to 1 mm and occasionally slightly curves backwards and/or to one side. Towards the base peduncle again slightly thickens.

*Color (immediately below spathe).*—Front: between 144 A (yellow-green), 143 A and 137 C–D (both green). Back: 144 A (yellow-green).

*Stipe.*—0.6–1.2 cm long, 3.0–4.5 mm in diameter.

Spathe:

*Shape.*—Deeply cupped; wide elliptic with some ovate tendencies; tip acuminate with aristate tendencies, curled; base obtuse with cuneate tendencies, decurrent on peduncle, in most spathes slightly asymmetric (difference in length between the two lobes usually less than 5 mm).

*Size.*—9.6–14.7 cm long by 5.9–7.8 cm wide and 1.9–2.8 cm deep; length:width ratio 1.5–1.9:1.

*Color.*—155 D, B (white) with various amounts of green on both sides. On the back side green coloration is more pronounced than on the front. It extrapolates from peduncle into a green stripe along them idrib and tapers to approximately 1.5–2.0 mm wide about mid length of the spathe; more distally the green stripe becomes less defined as the color becomes somewhat diffused; toward the tip the green zone widens to occupy the entire tip except for the spathe margins. A few lateral veins or their fragments are also green. Green coloration comprises of different shades of and between 144 A–B (yellow-green), 143 A–B (green) and 137 C–D (green). In the proximal half of the spathe the entire stripe is dark green (closest to 137 C), in the distal half this dark color is confined to the midrib and the tip. Areas adjacent to midrib as well as lateral veins are much lighter and more yellow (closest to 144 A–B). On the front side the tip and distal approximately ¼ to ⅓ of the midrib is a mixture of: 146 A–B, 144 A (both yellow-green), 143 A–B, 141 A–B, 137 A–B (all three green); the size of green color area at the tip and its intensity varies from spathe to spathe.

Spadix:

*Size.*—4.3–6.2 cm long; 1.7–1.9 cm in diameter.

*Color.*—Between 158 B and 158 C (yellow-white).

Botanical flower:

*Perianth.*—Inconspicuous, segments united.

*Pistil.*—Large, thick, acute, extrudes 3–4 mm beyond perianth, stigma large.

*Stamens.*—Produce little to no pollen depending on the season.

Flowering: Continuous year-round natural flowering in 15 cm pots begins about 7–9 months from planting tissue culture produced microcuttings; after about 12 months two to six white spathes constantly present above foliage.

Spathe longevity: Spathe remains white for up to 5 weeks following bud emergence above foliage and then gradually changes to a green color.

Roots: Numerous, very thick, fleshy, white roots, lateral roots not very abundant.

Disease and insect resistance: No unusual susceptibility to diseases or insects noted to date.

Comparison with the Known Cultivars

The new cultivar can be compared to the known cultivar 'Petite'. Observations for comparisons were made on plants grown under similar conditions in a greenhouse near Altha, Fla.

'S12' is distinguished from 'Petite' by its more vigorous growth; earlier branching; more open growth habit; darker, thicker, more glossy and larger leaf blades; wider and more ovate spathes; thicker spadix, larger pistils and stigmas; earlier and more abundant natural flowering; better quality of first inflorescences; less pollen production.

I claim:

1. A new and distinct cultivar of Spathiphyllum plant named 'S12' substantially as described and illustrated herein, characterized particularly as to novelty by its medium size; relatively open growth habit; vigorous growth; early, abundant, year-round natural flowering; dark green, glossy, thick leaves; good quality inflorescence from near onset of flowering; strong thick peduncles on mature shoots; relatively large spathes with prominent spadixes, large pistils and stigmas and limited pollen production.

* * * * *